Figure 1:
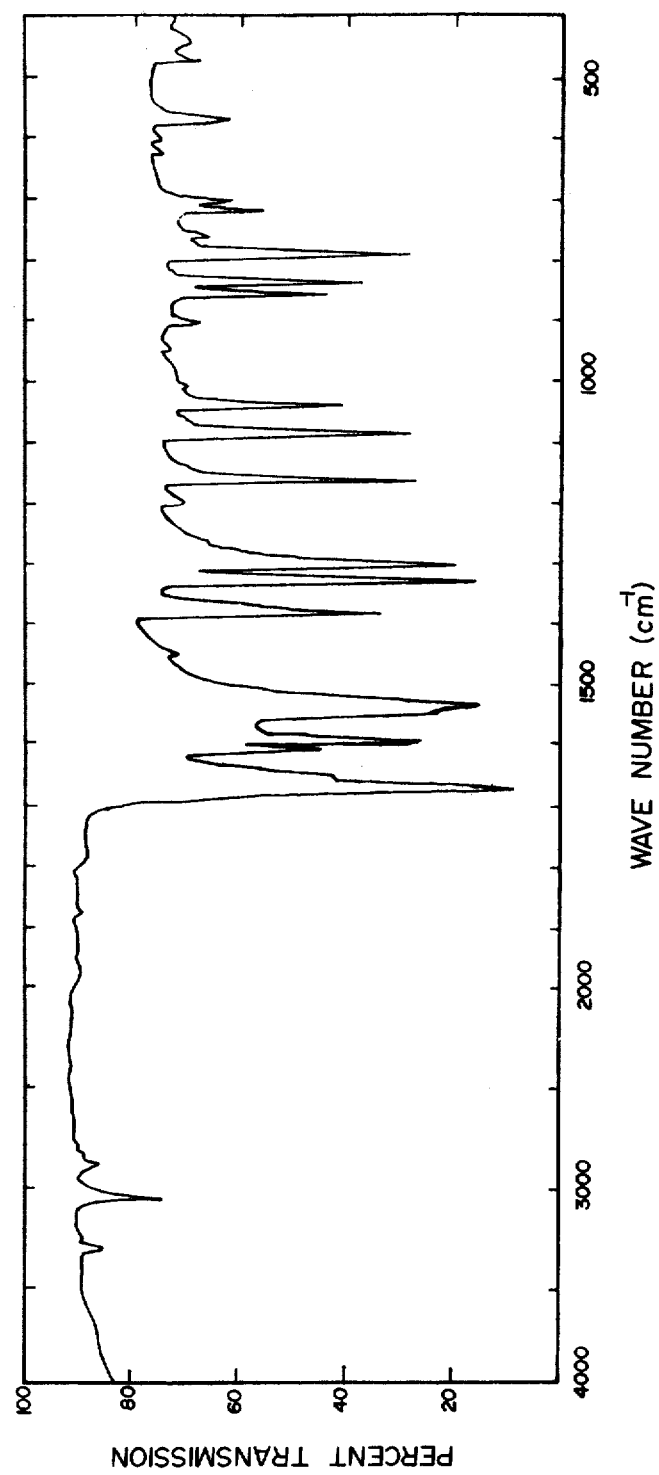

United States Patent [19]
Koike et al.

[11] 3,941,815

[45] Mar. 2, 1976

[54] PROCESS FOR THE PREPARATION OF 5-NITRO-1,4-NAPHTHOQUINONE

[75] Inventors: Hiroshi Koike, Takatsuki; Akio Fukui, Kyoto; Yuji Ito, Amagasaki; Takehiko Tanaka, Kobe; Yukio Okuda, Toyonaka, all of Japan

[73] Assignee: Nippon Shokubai Kagaku Kogyo Co., Ltd., Osaka, Japan

[22] Filed: July 31, 1974

[21] Appl. No.: 493,607

[30] Foreign Application Priority Data

| July 31, 1973 | Japan | 48-85458 |
| Oct. 22, 1973 | Japan | 48-117991 |
| Dec. 28, 1973 | Japan | 48-144649 |

[52] U.S. Cl. .............. 260/396 R; 260/369; 260/378
[51] Int. Cl.² ........................................ C07C 76/02
[58] Field of Search .......................... 260/396 R

[56] References Cited
UNITED STATES PATENTS
2,687,939  8/1954  Sartari .................. 260/396

FOREIGN PATENTS OR APPLICATIONS
1,135,083  11/1968  United Kingdom ............ 260/396 R OTHER PUBLICATIONS
Methoden der Organ. Chemie (Houben–Weyl), 4th Ed., 1971, X/I, p. 614.
De La Mare, Aromatic Substitution, (London), 1959, p. 63.

*Primary Examiner*—Vivian Garner
*Attorney, Agent, or Firm*—Armstrong, Nikaido & Wegner

[57] ABSTRACT

A process for the preparation of 5-nitro-1,4-naphthoquinone comprising nitrating 1,4-naphthoquinone under such a condition that the dehydrating value of sulfuric acid in the reaction mixture is at least 4 to selectively introduce a nitro group into the 5-position and pouring the reaction mixture into an aqueous medium to precipitate the product.

16 Claims, 2 Drawing Figures

PROCESS FOR THE PREPARATION OF 5-NITRO-1,4-NAPHTHOQUINONE

This invention relates to a process for the preparation of 5-nitro-1,4-naphthoquinone and, in particular, to an efficient process for the preparation of 5-nitro-1,4-naphthoquinone by direct nitration of 1,4-naphthoquinone in the presence of sulfuric acid.

5-Nitro-1,4-naphthoquinone is useful as a starting material for the production of dyes, pigments and agricultural chemicals. For instance, 1-nitroanthraquinone, an important intermediate for the synthesis of dyes, is obtainable by subjecting the 5-nitro-1,4-naphthoquinone to Diels-Alder reaction with butadiene and then to dehydrogenation. However, there is still unknown any industrially advantageous process for the production of 5-nitro-1,4-naphthoquinone in commercial scale.

It is generally known to obtain 1-nitroanthraquinone by nitrating anthraquinone with either nitric acid or a mixed acid of nitric acid and sulfuric acid, but it is unknown to produce 5-nitro-1,4-naphthoquinone by direct nitration of 1,4-naphthoquinone with such a mixed acid, or rather in "Methoden der Organischen Chemie," Vol. 10-1, page 614 (1971), edited by Eugen Müller, there is a description that "Nitration and nitrated products of 1,4-naphthoquinone are unknown." When an 2,3-unsubstituted-1,4-naphthoquinone is subjected to reaction with various reagents, there occurs no replacement reaction on benzenoid ring but occurs addition reaction to ethylenic linkage in quinonoid ring to form a 2-substituted- or 2,3-substituted-1,4-naphthoquinone, because, in 1,4-naphthoquinone constituted of a benzenoid ring and a quinonoid ring, the quinonoid ring is more unstable and reactive than the benzenoid ring. It is also known that, when an 1,4-naphthoquinone is subjected to direct nitration with nitric acid, there occur side reactions or decomposition because the quinonoid ring is easily oxidized. Such a compound as anthraquinone in which the quinonoid ring is protected in both sides by the benzenoid rings can be directly nitrated without any trouble due to unstability of a quinonoid ring. In West Germany Patent Specification No. 468,507, there is disclosed that a compound such as 2,3-dichloro-1,4-naphthoquinone in which the quinonoid ring is protected by substituents in the 2- and 3-position can be directly nitrated.

It was proposed to directly nitrate an 1,4-naphthoquinone by means of concentrated hydrofluoric acid and concentrated nitric acid, as disclosed in West Germany Patent Specification No. 1,247,288. However, it is difficult to put this process into practice in commercial scale since the nitration in the presence of concentrated hydrogen fluoride is dangerous in the working and destructive to the equipments.

Therefore, an object of the present invention is to provide a novel process for the preparation of 5-nitro-1,4-naphthoquinone by the direct nitration of 1,4-naphthoquinone.

Another object of the present invention is to provide an industrially advantageous process for the preparation of 5-nitro-1,4-naphthoquinone with no accompanying difficulty and danger in the working thereof.

A further object of the present invention is to provide a process for producing 5-nitro-1,4-naphthoquinone of a high purity in a high yield by direct nitration of 1,4-naphthoquinone.

In accordance with the present invention, 5-nitro-1,4-naphthoquinone is obtained by nitrating 1,4-naphthoquinone with nitric acid in the presence of sulfuric acid under such a condition that the dehydrating value of sulfuric acid is at least 4 and then pouring the reaction mixture into an aqueous medium to precipitate the product.

It seems surprising to us that 5-nitro-1,4-naphthoquinone is obtained advantageously in a high yield, contrary to common knowledge, by nitrating 1,4-naphthoquinone with nitric acid when the nitration is carried out under such a selected condition that the dehydrating value of sulfuric acid is at least 4, even though the 1,4-naphthoquinone is not protected in the 2- and 3-position at all. That is, water contained in the reaction system has an adverse effect on the selectivity of the reaction and, when significant quantity of water is present in the reaction system, there is little obtained the desired 5-nitro-1,4-naphthoquinone. The reaction mixture thus obtained is then poured into an aqueous medium to obtain 5-nitro-1,4-naphthoquinone.

Figure 2:
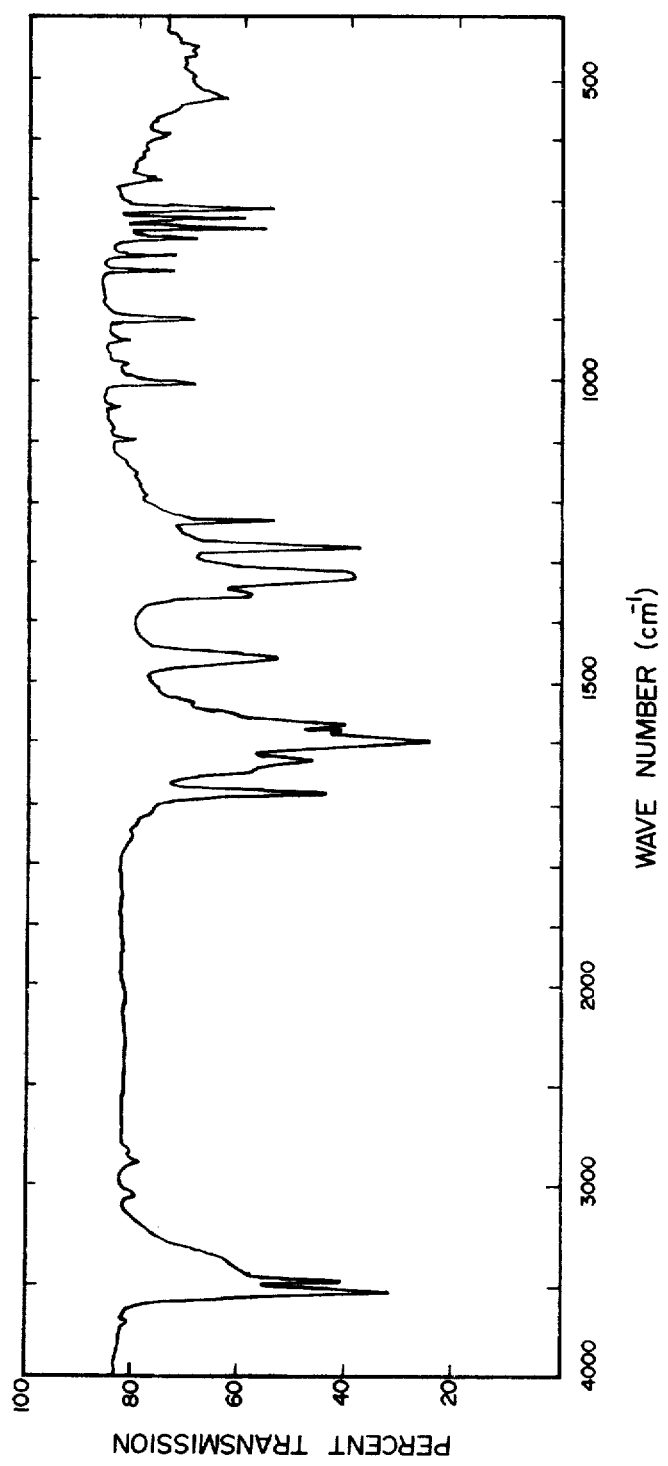

The present invention will be understood best in connection with the accompanying drawings wherein;

FIG. 1 illustrates a chart of infrared absorption spectrum of the 5-nitro-1,4-naphthoquinone obtained by the process of the present invention, and FIG. 2 illustrates the chart of the infrared absorption spectrum of a product formed by reaction of its quinonoid ring by nitration under the condition of less than 4 of dehydrating value of sulfuric acid.

The term "Dehydrating Value of Sulfuric acid" as used in this specification (hereinafter referred to as "D.V.S.)" indicates the weight ratio of the total sulfuric acid to the total water in the reaction system of the nitration of 1,4-naphthoquinone by mixed acid and is represented by the following equation:

$$D.V.S. = \frac{\text{Total weight of sulfuric acid in the reaction system}}{\text{Total weight of water in the reaction system}}$$

The nitration of 1,4-naphthoquinone carried out in sulfuric acid that plays a role as solvent in accordance with the present invention should be conducted to a D.V.S. of at least 4, preferably of at least 6. Because, when the D.V.S. of the reaction system is less than 4, water in the system decreases the selectivity of the reaction and effects side-reactions to such a great extent that there is yielded substantially no end product 5-nitro-1,4-naphthoquinone. Sulfuric acid having a role of solvent is used in an amount usually of 2 to 30 times the weight of 1,4-naphthoquinone, preferably of 2 to 20 times and more desirably of 3 to 10 times.

Further improvements in purity and yield of 5-nitro-1,4-naphthoquinone as the end product are attained by carrying out the nitration under a condition substantially free from free water. Such condition is realized by introducing sulfur trioxide into the reaction system. Namely, sulfur trioxide introduced into the reaction system maintains or increases the D.V.S. of the reaction system. Sulfur trioxide may be added in an amount of 0.0 to 1.2, preferably 0.01 to 0.6 times the weight of sulfuric acid. It is advantageous from an industrial point of view to use sulfur trioxide in such an amount as to have been substantially hydrated into sulfuric acid at the end of the reaction. Such a condition is realized by the use of oleum containing 1 to 60 percent by weight of sulfur trioxide. There may suitably be added sulfur trioxide or oleum in the reaction system during reaction.

In the process of the present invention nitric acid is used in an amount usually of 0.8 to 7 moles, preferably of 1 to 3 moles per mole of 1,4-naphthoquinone. As sources of nitric acid there may be used concentrated nitric acid of a specific gravity of at least 1.38, preferably fuming nitric acid. There may also be used nitrates capable of forming nitric acid in sulfuric acid and dinitrogen pentoxide.

The nitration in accordance with the present invention is accomplished by adding 1,4-naphthoquinone to cooled concentrated sulfuric acid and then adding thereto nitric acid or a mixed acid of nitric acid and sulfuric acid or, alternatively, by adding 1,4-naphthoquinone to such a mixed acid, the latter procedure being preferable. The reaction may be carried out batch-wise or in continuous manner as a tubular reactor method. The reaction may be carried out at a temperature of $-20°$ to $+80°C$, preferably $0°$ to $+60°C$. The reaction time varies widely depending on the reaction temperature, for instance, several hours at $15°$ to $20°C$ and few minutes at $55°$ to $60°C$.

The reaction mixture thus obtained is poured into an aqueous medium, e.g. water, diluted sulfuric acid or diluted mixed acid, maintained at a temperature of $0°$ to $100°C$, preferably of $20°$ to $80°C$ and more preferably of $30°$ to $70°C$ to precipitate the product 5-nitro-1,4-naphthoquinone. The precipitate is filtered and washed with water. Attention should be given to the fact that occasionally there occurs deposition of crystals on the surface of the said poured liquid mixture, it being difficult to sufficiently disperse the deposit by agitation, to form lumps of the deposit occluding the mixed acid therein. On this occasion, there occur various undesirable successive reactions to bring about deterioration and decrease in yield of the end product 5-nitro-1,4-naphthoquinone because heat of dilution of the mixed acid occluded is not quickly eliminated.

The higher the concentration of 5-nitro-1,4-naphthoquinone in the reaction mixture is, the more the undesirable phenomena are liable to occur at a concentration of 10 percent by weight and tend to become remarkable at concentrations exceeding 15 percent by weight. Then we have found that, in the practice of the present invention, it is preferable to carry out the precipitation at temperatures of $20°$ to $80°C$ to eliminate such troubles. In accordance with the usual way it seems necessary to maintain the temperature not exceeding room temperature as to prevent the product from being subjected to high temperature. However the precipitation of crystals in accordance with the present invention from the nitration mixture especially of a high concentration of at least 15 percent by weight preferably is carried out at temperatures above room temperature, and more desirably it is carried out maintaining a precipitation temperature in the range of $30°$ to $70°C$ eliminating heat of dilution of sulfuric acid. But the precipitation must be carried out at a temperature of less than $100°C$, because the nitrated product thus formed is decomposed remarkably at a temperature of more than $100°C$.

As the aqueous medium to be added with the reaction mixture, there may be used a waste acid recovered from the nitration step besides aforesaid water, diluted sulfuric acid and diluted mixed acid. The aqueous medium may be used in an amount of 3 to 50, preferably 5 to 30 times the weight of the reaction mixture supplied.

The 5-nitro-1,4-naphthoquinone thus obtained is useful as a starting material for the manufacture of dyes, pigments and agricultural chemicals. 1-Nitroanthraquinone which is important as an intermediate of various dyes may be obtained by addition of butadiene to 5-nitro-1,4-naphthoquinone and following dehydrogenation, and 1-aminoanthraquinone by subsequent reduction of the dehydrogenated product. This method of preparing 1-amino-anthraquinone is advantageous compared with a prior method in which first anthraquinone is sulfonated in the presence of mercury catalyst in that this method needs no mercury catalyst and yields no disubstituted product as is yielded in nitration of anthraquinone.

EXAMPLE 1

A 100 ml four-necked glass flask equipped with a silica gel-packed dryer tube, a thermometer and a stirrer was charged with 70 g of a mixed acid of a D.V.S. of 21.3 consisting of 11 percent by weight of nitric acid, 85 percent by weight of sulfuric acid and 4 percent by weight of water. After cooled to $5°$ to $10°C$, the mixed acid was added with 10.0 g of 1,4-naphthoquinone. The mixture was maintained at $15°$ to $20°C$ for 3 hours with stirring to effect reaction. The D.V.S. of the mixture after completion of reaction was 15.0. A 1,000 ml four-necked glass flask equipped with a thermometer, a stirrer and a dropping funnel was charged with 700 ml of water, then added dropwise the reaction mixture thus obtained thereto while maintaining at $18°C$ to precipitate a reaction product. The slurry was stirred for additional 30 minutes. The precipitate was then filtered by means of a G-3 glass filter, washed with water, washed with 20 g of a 50 percent aqueous methanol and dried under reduced pressure to obtain 11.3 g of a yellow-colored product. The crude product had a melting point of $153°C$. The crude product was recrystallized from methanol to obtain 5-nitro-1,4-naphthoquinone of a melting point of $167°C$.

The recrystallized product was identified to be 5-nitro-1,4-naphthoquinone by elementary analysis and infrared absorption spectrum analysis and, in addition, by N.M.R. spectrum analysis.

The results of elementary analysis on the product were as follows:
Found C 59.20 %, H 2.49 %, N 6.93 %
Theoretical C 59.12 %, H 2.48 %, N 6.90 %.

The infrared absorption spectrum of the product was as shown in FIG. 1.

EXAMPLE 2

The same procedure as in Example 1 was repeated except that the mixture of the mixed acid and 1,4-naphthoquinone was heated to $55°C$ in 5 minutes, maintained at $55°$ to $58°C$ for 5 minutes and then quickly cooled to $10°C$. There was obtained a crude 5-nitro-1,4-naphthoquinone of a melting point of $150°C$ in a yield of 10.5 g. The crude product was purified in the same manner as in Example 1 to obtain the same results with Example 1.

EXAMPLE 3

In the same apparatus as in Example 1, 10.0 g of 1,4-naphthoquinone was added to 35 g of a 98 percent sulfuric acid at a temperature of $5°$ to $10°C$, then dropped thereinto 35 g of a mixed acid consisting of 74 percent by weight of sulfuric acid, 22 percent by weight of nitric acid and 4 percent by weight of water over 1 hour with stirring and maintaining the reaction temperature at 15° to 20°C. The reaction mixture was then maintained at 15° to 30°C for 3 hours and then processed in the same manner as in Example 1. The D.V.S. of the mixture was 28.7 before reaction and 18.6 after reaction. The yield of the crude 5-nitro-1,4-naphthoquinone was 10.0 g and the melting point was 144°C. The crude product was purified to obtain the same results as in Example 1.

EXAMPLE 4

The same procedure as in Example 1 was repeated except that 10.0 g of 1,4-naphthoquinone was added to 200 g of a mixed acid consisting of 83 percent by weight of sulfuric acid, 4 percent by weight of nitric acid and 13 percent by weight of water with maintaining a temperature of 5° to 10°C, to obtain 8.9 g of brown-colored crude 5-nitro-1,4-naphthoquinone of a melting point of 140°C. The D.V.S. of the reaction mixture after reaction was 6.1. The crude product was purified to obtain the similar results with Example 1.

COMPARATIVE EXAMPLE 1

A 200 ml four-necked glass flask equipped with a silica gel-packed dryer tube, a thermometer and stirrer was charged with 200 g of a mixed acid of a D.V.S. of 3.8 consisting of 76 percent by weight of sulfuric acid, 4 percent by weight of nitric acid and 20 percent by weight of water. 10.0 g of 1,4-naphthoquinone was added to the mixed acid as in Example 1 and the reaction mixture was stirred at 15° to 20°C for 3 hours. After the reaction, the D.V.S. of the reaction system was 3.7. The reaction mixture was then poured into 500 g of water to precipitate a reaction product at a temperature of 18°C. After stirring for 30 minutes, the reaction product was filtered, washed with water and dried under reduced pressure to obtain 1.5 g of a brown-colored elastomeric product. This product was proved not to be 5-nitro-1,4-naphthoquinone by infrared absorption spectrum analysis. The main proudct contained in the filtrate was a water-soluble matter. A product obtained by salting out the filtrate and extracting with ethyl acetate was subjected to reading of the infrared absorption spectrum. The result was as shown in FIG. 2. The product was confirmed to be a compound formed by reaction of a quinonoid ring in the naphthoquinone by N.M.R. spectrum analysis.

EXAMPLE 5

In the same apparatus as in Example 1, 20 g of 1,4-naphthoquinone was stirred into 80 g of a mixed acid of a D.V.S. of 19.0 consisting of 76 percent by weight of sulfuric acid, 20 percent by weight of nitric acid and 4 percent by weight of water while maintaining the temperature of the system at 0° to 5°C. The reaction temperature was gradually raised to 15°C over 30 minutes and then maintained at 15°C for 3 hours. After completion of reaction, the D.V.S. of the system was 11.0. The reaction mixture was stirred over 5 minutes into 400 ml of water to precipitate crystals while cooling the water as to maintain its temperature at 40°C. After completion of pouring of the reaction mixture, the liquid temperature was lowered to 25°C. The state of dispersion of the precipitated crystals was good.

The crystals were filtered, washed twice with 100 ml of water and dried under reduced pressure to obtain 22.1 g of 5-nitro-1,4-naphthoquinone of a melting point of 154°C. The crystals were of nearly equal particle size not exceeding 0.2 mm. The amount of acidic matter remaining in the crystals was 0.3 percent by weight calculated in sulfuric acid equivalent.

EXAMPLE 6

In the same apparatus as in Example 1, 10.0 g of 1,4-naphthoquinone was dissolved, with stirring, in 60 g of a mixed acid consisting of 74 percent by weight, of sulfuric acid 11 percent by weight of nitric acid and 15 percent by weight of sulfur trioxide, the mixed acid being maintained at 0° to 5°C. The reaction mixture was then maintained at 15° to 20°C for 3 hours and thereafter added to 700 g of water to precipitate a reaction product at a temperature of 40°C. The slurry thus formed was stirred for 30 minutes to complete precipitation, then filtered, washed with water and then with 20 g of methanol and dried under reduced pressure to obtain 11.4 g of a yellow-colored crude product of a melting point of 155°C. The crude product was recrystallised from an 1:1 acetone-methanol mixture to obtain 5-nitro-1,4-naphthoquinone of a melting point of 167°C. The results of elementary analysis, infrared absorption spectrum analysis and N.M.R. absorption spectrum analysis were the same as in Example 1.

EXAMPLE 7

The same procedure as in Example 6 was repeated except that the reaction temperature was raised to 55°C in 5 minutes after addition of 1,4-naphthoquinone, maintained at 55° to 58°C 5 minutes and immediately lowered to 10°C, to obtain 10.7 g of crude 5-nitro-1,4-naphthoquinone of a melting point of 152°C. The crude product was purified in the same manner as in Example 6 to obtain the same result as in Example 1.

EXAMPLE 8

In the same apparatus as in Example 1, 10.0 g of 1,4-naphthoquinone was added to 40 g of fuming sulfuric acid of a sulfur trioxide content of 20 percent maintained at 0° to 5°C, then added thereto 30 g of a mixed acid consisting of 70 percent by weight of sulfuric acid, 25 percent by weight of nitric acid and 5 percent by weight of water dropwise over 1 hour while maintaining the reaction temperature at 15° to 20°C. The reaction mixture was maintained at 15° to 20°C for additional 3 hours and then processed in the same manner as in Example 6 to obtain 11.0 g of crude 5-nitro-1,4-naphthoquinone of a melting point of 153°C. The crude product was purified in the same manner as in Example 6 to obtain the same result as in Example 1.

EXAMPLE 9

In the same apparatus as in Example 1, 20 g of 1,4-naphthoquinone was added, with stirring, to 70 g of a mixed acid consisting of 66 percent by weight of sulfuric acid, 19 percent by weight of nitric acid and 15 percent by weight of sulfur trioxide while maintaining the mixed acid at 0° to 5°C. The temperature of the mixture was gradually raised to 15°C over 30 minutes and maintained at 15°C for 3 hours to complete reaction. The reaction mixture was then stirred into 400 ml of water at 20°C in 5 minutes to precipitate crystals, while cooling the water as to maintain a liquid temperature at 40°C. The state of dispersion of the precipitated crystals was good. The precipitate was processed in the same manner as in Example 5 to obtain 22.7 g of crude 5-nitro-1,4-naphthoquinone of a melting point of 155°C. The crystals were of a nearly equal particle size not exceeding 0.2 mm. The amount of acidic matter remaining in the crystals was 0.4 percent by weight in sulfuric acid equivalent.

EXAMPLE 10

In the same apparatus as in Example 1, 20 g of 1,4-naphthoquinone was stirred into 70 g of a mixed acid consisting of 70 percent by weight of sulfuric acid, 20 percent by weight of nitric acid and 10 percent by weight of sulfur trioxide, with cooling at 0° to 5°C. The reaction mixture was heated to 15°C over 30 minutes and then maintained at the temperature for 3 hours. The liquid reaction mixture was then stirred in 2 minutes into 400 ml of water at 20°C to precipitate crystals. During the precipitation, the liquid temperature reached the highest value of 68°C. The crystals were well dispersed during stirring. After completion of addition of the reaction mixture, the liquid temperature was quickly lowered by cooling to 35°C. The so precipitated crystals were separated, washed with water and dried in the same manner as in Example 5 to obtain 22.5 g of crude 5-nitro-1,4-naphthoquinone of a melting point of 153°C. The amount of acidic matter remaining in the crystals was 0.3 percent by weight in terms of sulfuric acid.

COMPARATIVE EXAMPLE 2

To 500 ml of water there was added 90 g of a liquid reaction mixture obtained by nitration under the same condition as in Example 9, with stirring over 10 minutes. The temperature of the reaction mixture was 15°C and the temperature of the precipitation system was maintained at 15° to 17°C by cooling. However, in this case, the reaction mixture deposited, as it was added to the precipitation medium, porous solid lumps on the wall of the precipitation vessel and on the blades of the stirrer. After completion of addition of the reaction mixture, stirring was continued to break up the lumps thereby to obtain pulverized crude 5-nitro-1,4-naphthoquinone of yellowish brown in color containing a large amount of coarse particles. The precipitate was separated, washed with water and dried in the same manner as in Example 5 to obtain 21.0 g of crude 5-nitro-1,4-naphthoquinone of a melting point of 149°C. The amount of acidic matter remaining in the solid product was 1.7 percent by weight in terms of sulfuric acid.

EXAMPLE 11

The same procedure as in Example 1 was repeated except that 10.0 g of 1,4-naphthoquinone was added to 100 g of a mixed acid consisting of 86 percent by weight of sulfuric acid, 10 percent by weight of sodium nitrate and 4 percent by weight of water while maintaining the temperature of the mixture at 5° to 10°C. The D.V.S. of the system was 21.5 before reaction and 16.7 after reaction. There was obtained 11.2 g of a yellow-colored product of a melting point of 153°C. By purification, there was obtined the same result as in Example 1.

What is claimed is:

1. A process for the preparation of 5-nitro-1, 4-naphthoquinone comprising nitrating 1,4-naphthoquinone with nitric acid in the presence of sulfuric acid at a temperature of −20°C to +80°C and under the condition that the weight ratio of the total amount of sulfuric acid to the total amount of water in the reaction system is at least 4 and adding the resulting reaction mixture to an aqueous medium to precipitate the product.

2. A process of claim 1 in which the dehydrating value of sulfuric acid is at least 6.

3. A process of claim 1 wherein sulfur trioxide is introduced into the reaction system during nitration.

4. A process of claim 3 wherein the amount of sulfur trioxide is up to 1.2 times the weight of sulfuric acid.

5. A process of claim 1 in which sulfuric acid is used in an amount of 2 to 30 times the weight of 1,4-naphthoquinone.

6. A process of claim 1 in which sulfuric acid is used in an amount of 2 to 20 times the weight of 1,4-naphthoquinone.

7. A process of claim 1 in which sulfuric acid is used in an amount of 3 to 10 times the weight of 1,4-naphthoquinone.

8. A process of claim 1 in which nitric acid is used in an amount of 0.8 to 7 moles per mole of 1,4-naphthoquinone.

9. A process of claim 1 in which nitric acid is used in an amount of 1 to 3 moles per mole of 1,4-naphthoquinone.

10. A process of claim 1 in which 1,4-naphthoquinone is added to a mixture of sulfuric acid and nitric acid.

11. A process of claim 1 in which the nitration is carried out at a temperature of 0°C to +60°C.

12. A process of claim 1 in which the precipitation of the nitration product is carried out at a temperature of 0°C to 100°C.

13. A process for the preparation of 5-nitro-1,4-naphthoquinone comprising nitrating 1,4-naphthoquinone at a temperature of 0° to 60°C by nitric acid in an amount of 0.8 to 7 moles per mole of 1,4-naphthoquinone in the presence of sulfuric acid in an amount of 2 to 30 times the weight of 1,4-naphthoquinone while keeping the weight ratio of the total amount of sulfuric acid to the total amount of water in the reaction system at a value of at least 6 and adding the reaction mixture thus obtained to an aqueous medium to precipitate the product at a temperature of 30° to 70°C.

14. A process of claim 13 wherein sulfur trioxide is introduced into the reaction system during nitration.

15. A process of claim 14 wherein the amount of sulfur trioxide is up to 1.2 times the weight of sulfuric acid.

16. A process of claim 13 in which 1,4-naphthoquinone is added to a mixture of sulfuric acid and nitric acid.

* * * * *